(12) United States Patent
Giannoudis et al.

(10) Patent No.: US 9,050,114 B2
(45) Date of Patent: Jun. 9, 2015

(54) SURGICAL IMPLANT

(76) Inventors: Peter Giannoudis, Leeds (GB); George Anastopoulos, Athens (GR)

(*) Notice: Subject to any disclaimer, the term of this patent is extended or adjusted under 35 U.S.C. 154(b) by 444 days.

(21) Appl. No.: 13/499,210

(22) PCT Filed: Sep. 27, 2010

(86) PCT No.: PCT/GB2010/001808
§ 371 (c)(1),
(2), (4) Date: Jun. 13, 2012

(87) PCT Pub. No.: WO2011/039502
PCT Pub. Date: Apr. 7, 2011

(65) Prior Publication Data
US 2012/0245642 A1 Sep. 27, 2012

(30) Foreign Application Priority Data

Sep. 29, 2009 (GB) .................................. 0917014.3
Apr. 23, 2010 (GB) .................................. 1006778.3

(51) Int. Cl.
*A61B 17/80* (2006.01)
*A61B 17/17* (2006.01)
*A61B 17/72* (2006.01)

(52) U.S. Cl.
CPC ......... *A61B 17/1725* (2013.01); *A61B 17/7233* (2013.01); *A61B 17/1764* (2013.01); *A61B 2017/1778* (2013.01)

(58) Field of Classification Search
CPC ........... A61B 17/7233; A61B 17/7225; A61B 17/7241; A61B 17/7283; A61B 17/8004
USPC ................................................ 606/62, 64–67
See application file for complete search history.

(56) References Cited

U.S. PATENT DOCUMENTS

| 6,355,041 | B1 | 3/2002 | Martin |
| 2002/0143337 | A1 | 10/2002 | Orbay et al. |
| 2003/0073999 | A1 | 4/2003 | Putnam |
| 2005/0085824 | A1 | 4/2005 | Castaneda |
| 2006/0015123 | A1 | 1/2006 | Fencl et al. |
| 2006/0149257 | A1 | 7/2006 | Orbay et al. |
| 2006/0161156 | A1* | 7/2006 | Orbay .......................... 606/62 |

(Continued)

FOREIGN PATENT DOCUMENTS

| EP | 0 468 192 | 1/1992 |
| EP | 1 330 988 | 7/2003 |

(Continued)

OTHER PUBLICATIONS

International Search Report dated May 23, 2011 issued in corresponding International Application No. PCT/GB2010/001808.

(Continued)

*Primary Examiner* — Andrew Yang
*Assistant Examiner* — Olivia C Chang
(74) *Attorney, Agent, or Firm* — Lempia Summerfield Katz LLC

(57) ABSTRACT

The invention relates to a surgical implant (10), and in particular, to a surgical implant for stabilizing a bone fracture (20). The surgical implant (10) comprising a plate (14) and an elongate member (16) projecting from the plate (14). The elongate member (16) is provided for insertion into a bone (32) and the plate (14) is provided for attachment to a surface of a bone (24). Each of the elongate member (16) and the plate (14) are provided with at least one fastening region for fastening the surgical implant (10) to the bone (24, 32).

9 Claims, 11 Drawing Sheets

(56) References Cited

U.S. PATENT DOCUMENTS

| | | |
|---|---|---|
| 2006/0189996 A1 | 8/2006 | Orbay et al. |
| 2007/0213727 A1* | 9/2007 | Bottlang et al. .............. 606/69 |
| 2007/0276401 A1 | 11/2007 | Choe et al. |
| 2009/0069812 A1 | 3/2009 | Gillard et al. |
| 2009/0093813 A1 | 4/2009 | Elghazaly |

FOREIGN PATENT DOCUMENTS

| | | |
|---|---|---|
| EP | 1 418 855 | 10/2005 |
| EP | 1 661 525 | 5/2006 |
| EP | 1 809 186 | 7/2007 |
| EP | 1 952 776 | 8/2008 |
| WO | WO 2005/044121 | 5/2005 |
| WO | WO 2006/050507 | 5/2006 |
| WO | WO 2007/086854 | 8/2007 |
| WO | WO 2009/042783 | 4/2009 |

OTHER PUBLICATIONS

Search Report dated Nov. 30, 2010 issued in related Great Britain Application No. 1016171.9.

Search Report dated Jan. 28, 2011 issued in Great Britain Application No. 1016171.9.

* cited by examiner

US 9,050,114 B2

SURGICAL IMPLANT

RELATED APPLICATION DATA

This U.S. national phase application is based on International Application No. PCT/GB2010/001808 filed on Sep. 27, 2010, which claimed priority to Great Britain Patent Application No. 0917014.3 filed on Sep. 29, 2009 and Great Britain Patent Application No. 1006778.3 filed on Apr. 23, 2010. Priority benefit of these earlier filed applications is hereby claimed, and the full disclosures of these earlier filed applications are hereby incorporated by reference herein.

TECHNICAL FIELD

The invention relates to a surgical implant, and in particular, to a surgical implant for stabilising a bone fracture.

BACKGROUND

A bone fracture of a bone such as a Tibia, a Humerus or a Femur may require treatment with a surgical implant. An orthopaedic surgeon may operate on the bone and may use the surgical implant for recreating the normal anatomy of the bone by a process known as reduction. Such reduction may be closed reduction or open reduction which relates to how bone fragments of the fractured bone are relocated. Open reduction involves surgically exposing the bone fragments by dissecting the tissues surrounding the bone fracture. Closed reduction involves manipulation of the bone fragments without significant surgical exposure. Closed reduction typically results in an improved patient recovery time when compared to open reduction due to a reduced invasive surgery of the tissue surrounding the bone fracture. The purpose of the surgical implant is to stabilise the fracture and maintain the reduction whilst the bone heals.

A bone such as the Tibia, the Humerus or the Femur comprises three main areas which are a Diaphysis region, a Metaphysis region and an Epiphysis region. The Diaphysis region is the main shaft or mid section of the bone. The Metaphysis region is the wider portion of the bone adjacent to the Diaphysis region. The Epiphysis region is the rounded end of the bone. It will be appreciated that the bone fracture may be located at any part of the bone and in any of these regions of the bone. Typically bone fractures occurring at or adjacent to an end of the bone are more problematic to treat due to the complication of being near to a joint, which has a more complicated structure.

It is known to provide an elongate plate to stabilise a bone fracture which is typically positioned by open reduction. The elongate plate has holes along its length for receiving bone screws to secure it to a surface of the bone. Such plates are usually used for treating mid-shaft Diaphyseal bone fractures and may be used for stabilising a bone fracture at or adjacent to an end of the bone. Typically the plate must be used with open reduction which means that the patient has a consequential longer recovery time. Furthermore, fitting the plate near to a joint may limit the movement of the joint in the future. Overall the elongate plate is awkward to use for bone fractures at or adjacent to an end of the bone.

SUMMARY

What is required is a way of permitting a bone fracture to be stabilised, which may reduce or minimise at least some of the above-mentioned problems.

According to a first aspect of the invention, there is provided a surgical implant for a bone fracture comprising a plate and an elongate member projecting from the plate, the elongate member for insertion into a bone and the plate for attachment to a surface of a bone, wherein each of the elongate member and the plate are provided with at least one fastening region for securing the surgical implant to a bone.

Such a surgical implant provides the advantage that it may be readily used to stabilise a fracture at or towards an end of a bone. The elongate member may be inserted into a bone via a relatively small incision into the tissue surrounding the fracture and then secured in place with fixing means such as bone screws located through the at least one fastening region. Accordingly, the surgical implant may be positioned with closed reduction which may provide a consequential shorter recovery time for a patient.

Preferably the elongate member comprises at least a portion that is curved. The curved portion may be an arc of a circle or an ellipse. Preferably the curved portion has a radius of curvature of between 45-130 mm. Preferably the curved portion is a single curve lying in a single plane. Such a curved portion has the advantage of being able to be inserted into the bone so that it extends along the bone when the plate abuts a surface of the bone. Such a curved portion also allows the elongate member to be located in parts of the bone that may be difficult to reach.

The elongate member may project from the plate such that the single plane is perpendicular to the plate. This arrangement may be useful for a surgeon when positioning the surgical implant into a bone who may be able to approximately judge the angle of the elongate member by looking at the plate.

In one embodiment the elongate member projects from the plate such the single plane is at an angle of between 5°-30° from the plate. The elongate member may project from the plate such that the single plane is also at an angle of between 3°-7° from a longitudinal axis of the plate. Another way of stating this feature is that the single plane is at an angle of between 3°-7° from another plane which is perpendicular to the plate, said another plane being aligned with a longitudinal axis of the plate. These features may further permit the elongate member to be located in parts of the bone that may be difficult to reach.

Preferably the elongate member is between 40-130 mm in length. Such a length is suitable to treat bone fractures in an end region of bones such as the Tibia, the Humerus or the Femur.

Preferably the plate is between 1-5 mm thick. Such a thickness is suitable when securing the plate to a surface of the bone so that it does not protrude too much from the surface of the bone. In a preferred embodiment the plate is substantially 3 mm thick.

In one embodiment the plate is circular in shape. The plate may be domed. Such an arrangement may allow the plate to be located more readily onto a surface of the bone that may be curved, such as the Epiphysis region.

In another embodiment the plate has a rectangular shape. The rectangular shape may have a length of between 20-60 mm. The rectangular shape may have a width of between 10-30 mm. Such dimensions are a convenient size for location of the plate on a surface of the bone.

The elongate member may project from the plate such that the rectangular shape is in line with the elongate member. The elongate member may project from a middle region of the plate. The elongate member may project from one end of the plate. The at least one fastening region of the plate may be at another end of the plate. Such arrangements are useful for a surgeon when positioning the surgical implant into a patient. The features of the elongate member projecting from one end of the plate and the fastening region being at another end of the plate are advantageous because fasteners used for securing the plate the surface of the bone do not interfere with the elongate member.

Preferably the elongate member projects from the plate at an angle of between 10-50°. Preferably the elongate member projects from the plate at an angle of between 31-41°. Such projection of the elongate member from the plate is preferably in the single plane which is perpendicular to the plate, or at an angle of 5-30° from the plate. In the case of a curved elongate member such projection is a tangent of the curve at a point of contact with the plate. Such an angle is useful because it allows the surgeon to position the elongate member so that it may reach bone fractures adjacent to an end of the bone or in a region adjacent the joint.

The plate may include up to six fastening regions. The elongate member may include up to eight fastening regions. Provision of such a plurality of fastening regions is useful for the surgeon when positioning the insert who may use one or more of them to secure the surgical implant to a bone.

A first portion of the elongate member adjacent to the plate may have up to two fastening regions. A second portion of the elongate member adjacent to a free end of the elongate member may have up to six fastening regions. In one embodiment the elongate member has two fastening regions substantially at its free end. In another embodiment the elongate member has one fastening region substantially at its free end. Such arrangements may provide the advantage of allowing a first region of the elongate member to be secured to the bone, and the second region to stabilise fractures.

The at least one fastening region may be a threaded fastening region. Such a threaded fastening region provides the advantage that a fastener can be locked in position to the surgical implant.

In a preferred embodiment at least one of the fastening regions is a through hole for receiving a fastener. Such a fastener may be a bone screw, a percutaneous pin, or a transarticular pin.

Preferably the elongate member includes at least two through holes. Preferably the at least two through holes have respective axes which are non-parallel. Such non-parallel axes are a useful feature because it provides an improved fastening of the surgical implant to the bone. In one embodiment the respective axes are substantially perpendicular.

The at least two through holes may at least partially intersect each other. In a preferred embodiment the at least two through holes are substantially at the free end of the elongate member.

In a preferred embodiment the plate has at least one through hole and the elongate member has at least one through hole. Preferably the at least two through holes have respective axes which are non-parallel. Such non-parallel axes are a useful feature because it provides an improved fastening of the surgical implant to the bone.

At least one through hole in the elongate member may have an axis which is between 0°-70° from a normal to the elongate member. Preferably at least one through hole in the elongate member has an axis which is between 5°-70° from a normal to the elongate member. Preferably at least one through hole in the elongate member has an axis which is between 10°-70° from a normal to the elongate member. Such an angle of the axis may permit the surgical implant to be fastened to the bone in places which are awkward to reach. Such an angle also provides the surgeon with additional options for fastening the elongate member to the bone.

Preferably the surgical implant is provided as a unitary item. Such a unitary item is convenient to handle and position.

According to a second aspect of the invention there is provided a method of surgery to position a surgical implant for stabilising a bone fracture, the surgical implant comprising a plate and an elongate member projecting from the plate, each of the elongate member and the plate being provided with at least one fastening region, the method comprising:
  forming a hole in a surface of a bone;
  forming a canal inside the bone from the hole;
  inserting the elongate member into the canal so that the plate abuts a surface of the bone; and
  securing the surgical implant to the bone using each fastening region.

Such a method permits a bone fracture to be stabilised at or towards an end of a bone using a surgical implant. The elongate member may be inserted into a bone via a relatively small incision into the tissue surrounding the fracture, and then secured in place with fixing means such as bone screws located through the at least one fastening region. Inserting the elongate member in this manner permits the surgical implant to be positioned using closed reduction which may provide a consequential shorter recovery time for a patient.

Preferably the method further includes forming the canal in an end region of the bone. The end region is preferably an end one third region of the bone.

Preferably the method further includes fastening the plate to the surface of the bone prior to fastening the elongate member to the bone. Such a method may be a convenient way to position the surgical implant.

The method may further include inserting the surgical implant so that the elongate member extends towards the end of the bone. The method may further include inserting the surgical implant so that the elongate member extends away from the end of the bone. Such ways of positioning the surgical implant have the advantage of being able to stabilise bone fractures in parts of the bone that may be awkward to reach.

The method may further include making an incision in the soft tissue surrounding the fracture of between 20-40 mm in length prior to forming the hole in the bone. Such an incision is a relatively small incision for inserting a surgical implant which may provide the advantage of an improved patient recovery time.

The method may further include using a guide apparatus to determine an entry point for at least one fastener to secure the surgical implant to the bone. Such a guide apparatus may help to improve the securing of the surgical implant to the bone.

The method may further include using arthroscopic monitoring when securing the surgical implant to the bone.

The method may further include inserting a bone graft into the canal prior to inserting the surgical implant into the bone. Such a method provides versatility and an additional option when stabilising the bone fracture.

According to a third aspect of the invention there is provided a guide apparatus for positioning a surgical implant in a bone, comprising a body and a holding device for detachable connection of a surgical implant thereto, the body comprising at least one guide device for alignment with a part of a surgical implant.

Such a guide apparatus may help to improve the securing of the surgical implant to the bone.

Preferably the body is a planar body. The planar body may have a thickness of between 4-6 mm.

Preferably the holding device is a rod projecting from the body. Preferably the rod projects from the body so that it is substantially perpendicular to the planar body.

Preferably the at least one guide device is a tube which has a pre-defined orientation relative to the body.

The guide apparatus may further include a plurality of guide devices for alignment with a part of a surgical implant.

The guide apparatus may further include a pin for location in the at least one guide device for alignment with a part of a surgical implant.

The guide apparatus may further include a surgical implant detachably connectable to the holding device.

BRIEF DESCRIPTION OF THE DRAWINGS

Other features of the invention will be apparent from the following description of preferred embodiments shown by way of example only with reference to the accompanying drawings, in which.

DETAILED DESCRIPTION

FIGS. 1-5 show diagrams of similar surgical implants according to various embodiments of the invention and located in situ at proximal or distal regions of different bones. The similar surgical implants have different dimensions for treating bone fractures at or adjacent to the ends of the different bones.

Figure 1:
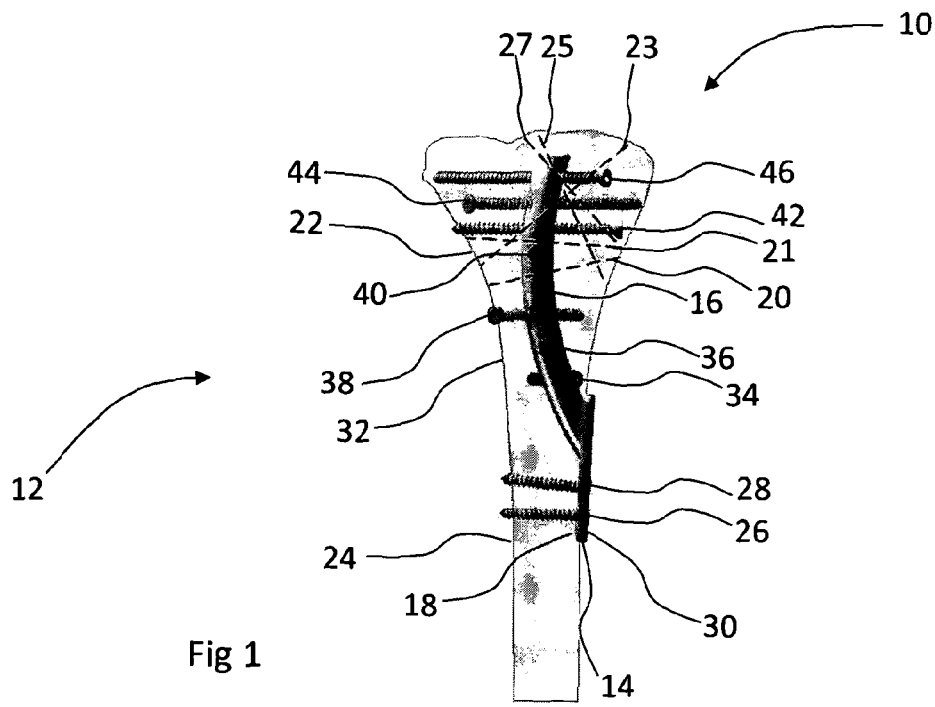
FIG. 1 shows a diagram of a surgical implant and a proximal tibia region according to an embodiment of the invention.

FIG. 1 shows a diagram of a surgical implant, generally designated 10, and a proximal tibia region, generally designated 12, according to an embodiment of the invention. In FIG. 1 the surgical implant 10 is shown to comprise a plate 14 and an elongate member 16. The elongate member 16 may be alternatively termed a nail or an intra-articular extension. The surgical implant 10 is manufactured from a material suitable for implantation into the human body, and may be made of titanium or an alloy based on titanium with a suitable surface treatment such as titanium oxide. Such a material is well known in the art and will not be described further. It will be appreciated that alternative materials may be used as appropriate with the requirement that they are suitable for implantation into the human body.

The plate 14 is connected to the elongate member 16. In the case of manufacturing the surgical implant 10 from titanium, the plate 14 is welded to the elongate member 16 at a connection end thereof such that the elongate member 16 has a free end. The plate 14 is a flat rectangular part which is 3 mm thick, 28 mm long and 16 mm wide. The connection end of the elongate member 16 is welded to a middle region of a first surface 18 of the plate 14 such that the elongate member 16 is in line with the plate 14.

The elongate member 16 is a curved bar of 60 mm in length and having a constant circular section. The curve forms, for example, an arc of a circle or an ellipse having a radius of curvature of about 55 mm. The curve is a single curve which lies in a single plane. The elongate member 16 is connected to the first surface 18 so that the plane of the curve is perpendicular to the plate 14. The elongate member 16 is connected to the first surface 18 so that a tangent of the curve of the elongate member 16 at the point of contact with the plate 14 is at an angle of 30°. In another arrangement the curved elongate member 16 lies in a single plane which is at an angle of between 5°-30° from the plate 14. This further assists with location of the insert 10 into the bone.

The surgical implant 10 is shown to be located in the proximal tibia region 12 which has a fracture indicate by a dashed line 20 in an Epiphysis region 22. The fracture 20 may be a tibial plateau fracture. Alternative or additional fractures are indicated at 21, 23, 25, 27. The plate 14 is secured in a Diaphysis region 24 of the proximal tibia region 12 by two bone screws 26, 28 which pass through respective holes in the plate 14, and which are inserted from a second surface 30 of the plate 14. It can be seen in FIG. 1 that the bone screws 26, 28 have different axes of insertion into the Diaphysis region 24 which provides an improved securing of the plate 14 to it. It can also be seen that the bone screws 26, 28 are at one end of the plate 14 and the elongate member 16 is connected to another end of the plate 14. This has the advantage that the bone screws 26, 28 do not interfere with the elongate member.

The elongate member 16 is shown to be positioned in the proximal tibia region 12 in an area spanning a Metaphysis region 32 and the Epiphysis region 22. A first portion of the elongate member 16 adjacent to the plate 14 has three holes for receiving three bone screws 34, 36, 38 to secure the surgical insert 10 to the Metaphysis region 32. A second portion of the elongate member 16 adjacent to its free end has four holes for receiving four bone screws 40, 42, 44, 46 to secure the surgical insert 10 to the Epiphysis region 22. In FIG. 1 it can be seen that the fracture 20 is located between the bone screws 34, 36, 38 of the first portion, and the bone screws 40, 42, 44, 46 of the second portion. It can also be seen that the axes of insertion of the bone screws 34, 36, 38, 40, 42, 44, 46 are all different such that the respective holes of the elongate member 16 for receiving the bone screws 34, 36, 38, 40, 42, 44, 46 also have different axes. Such an arrangement of holes in the elongate member 16 having different axes is a useful feature because it provides for a stronger fastening of the surgical implant 10.

Figure 2:
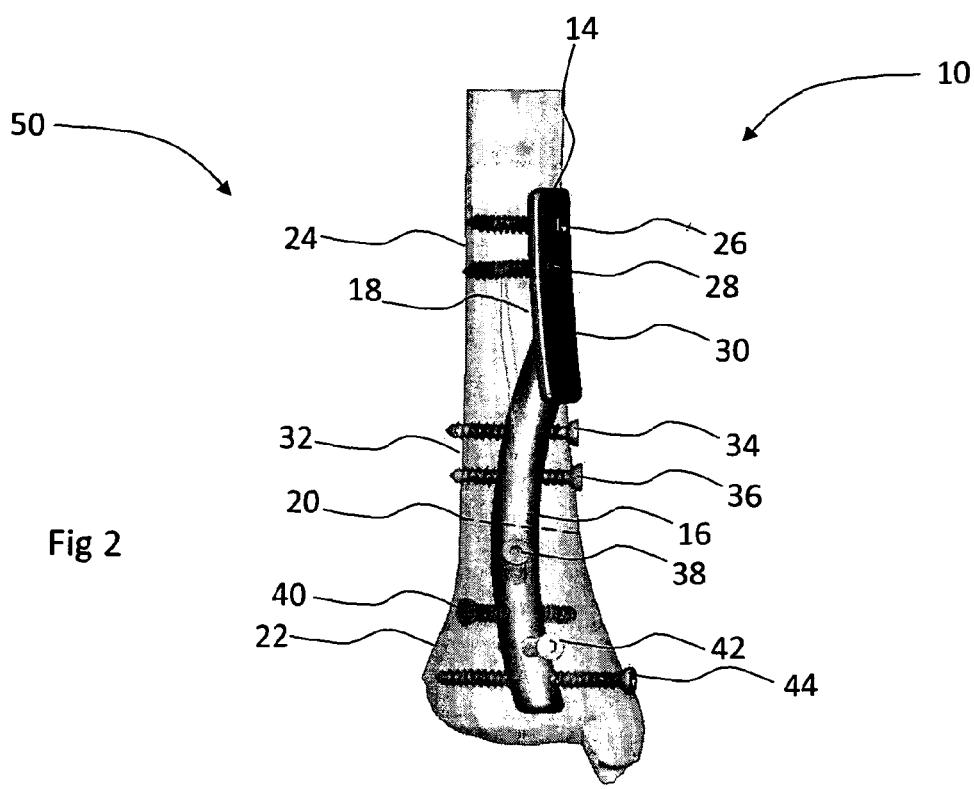
FIG. 2 shows a diagram of a surgical implant and a distal tibia region according to another embodiment of the invention.

FIG. 2 shows a diagram of a surgical implant, generally designated 10, and a distal tibia region, generally designated 50, according to another embodiment of the invention. In FIG. 2 like features to the arrangements of FIG. 1 are shown with like reference numerals. In FIG. 2 the elongate member 16 is shown to be positioned in the distal tibia region 50 in an area spanning the Metaphysis region 32 and the Epiphysis region 22. The plate 14 is secured in the Diaphysis region 24 of the distal tibia region 50 by two bone screws 26, 28 which pass through respective holes in the plate 14. A first portion of the elongate member 16 adjacent to the plate 14 has two holes for receiving two bone screws 34, 36 to secure the surgical insert 10 to the Metaphysis region 32. A second portion of the elongate member 16 adjacent to its free end has five holes for receiving five bone screws 38, 40, 42, 44 to secure the surgical insert 10 to the Epiphysis region 22. In FIG. 2 it can be seen that the fracture 20 is located between the bone screws 34, 36 of the first portion, and the bone screws 38, 40, 42, 44 of the second portion. The fracture 20 may be a pilon fracture. Alternative fractures may be present as per the fractures 21, 23, 25, 27 of FIG. 1 which have been omitted from FIG. 2 for the purposes of clarity.

The elongate member 16 shown in FIG. 2 is about 80 mm in length, and the plate is about 50 mm in length so that the combined length of the elongate member 16 and the plate 14 is about 120 mm in length. The curve of the elongate member 16 has a radius of curvature of about 120 mm. The curve is a single curve which lies in a single plane. The elongate member 16 is connected to the first surface 18 so that the plane of the curve is perpendicular to the plate 14. The elongate member 16 is connected to the first surface 18 so that a tangent of the curve of the elongate member 16 at the point of contact with the plate 14 is at an angle of 25°. In another arrangement the curved elongate member 16 lies in a single plane which is at an angle of between 5°-30° from the plate 14. This further assists with location of the insert 10 into the bone.

Figure 3:
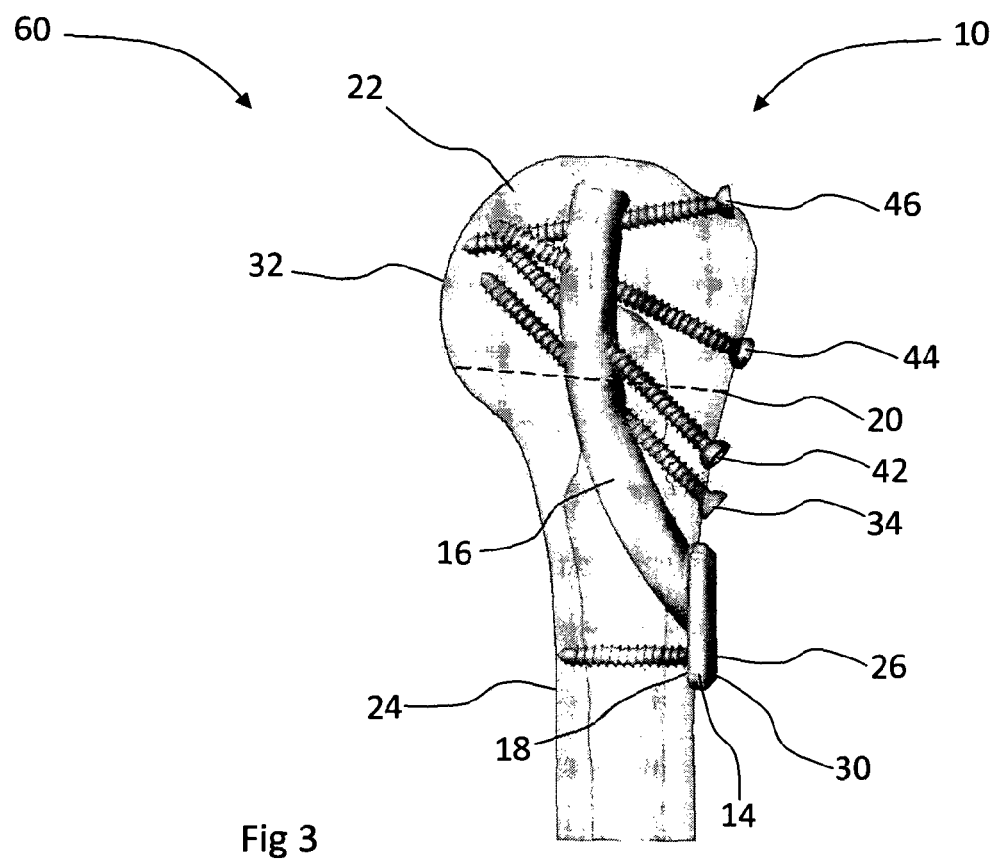
FIG. 3 shows a diagram of a surgical implant and a proximal humerus region according to an embodiment of the invention.

FIG. 3 shows a diagram of a surgical implant, generally designated 10, and a proximal humerus region, generally designated 60, according to an embodiment of the invention. In FIG. 3 like features to the arrangements of FIGS. 1 and 2 are shown with like reference numerals. In FIG. 3 the elongate member 16 is shown to be positioned in the proximal humerus region 60 in an area spanning the Metaphysis region 32 and the Epiphysis region 22. The plate 14 is secured in the Diaphysis region 24 of the proximal humerus region 60 by one bone screw 26 which passes through a hole in the plate 14. A first portion of the elongate member 16 adjacent to the plate 14 has one hole for receiving one bone screw 34 to secure the surgical insert 10 to the Metaphysis region 32. A second portion of the elongate member 16 adjacent to its free end has three holes for receiving three bone screws 42, 44, 46 to secure the surgical insert 10 to the Epiphysis region 22. In FIG. 3 it can be seen that the fracture 20 is located approximately between the bone screw 34 of the first portion, and the bone screws 42, 44, 46 of the second portion. The fracture 20 may be a proximal humerus to humerus head fracture. Alternative fractures may be present as per the fractures 21, 23, 25, 27 of FIG. 1 which have been omitted from FIG. 3 for the purposes of clarity.

The elongate member 16 shown in FIG. 3 is about 90 mm in length, and the plate is about 30 mm in length so that the combined length of the elongate member 16 and the plate 14 is about 110 mm in length. The curve of the elongate member 16 has a radius of curvature of about 80 mm. The curve is a single curve which lies in a single plane. The elongate member 16 is connected to the first surface 18 so that the plane of the curve is perpendicular to the plate 14. The elongate member 16 is connected to the first surface 18 so that a tangent of the curve of the elongate member 16 at the point of contact with the plate 14 is at an angle of 45°. In another arrangement the curved elongate member 16 lies in a single plane which is at an angle of between 5°-30° from the plate 14. This further assists with location of the insert 10 into the bone.

Figure 4:
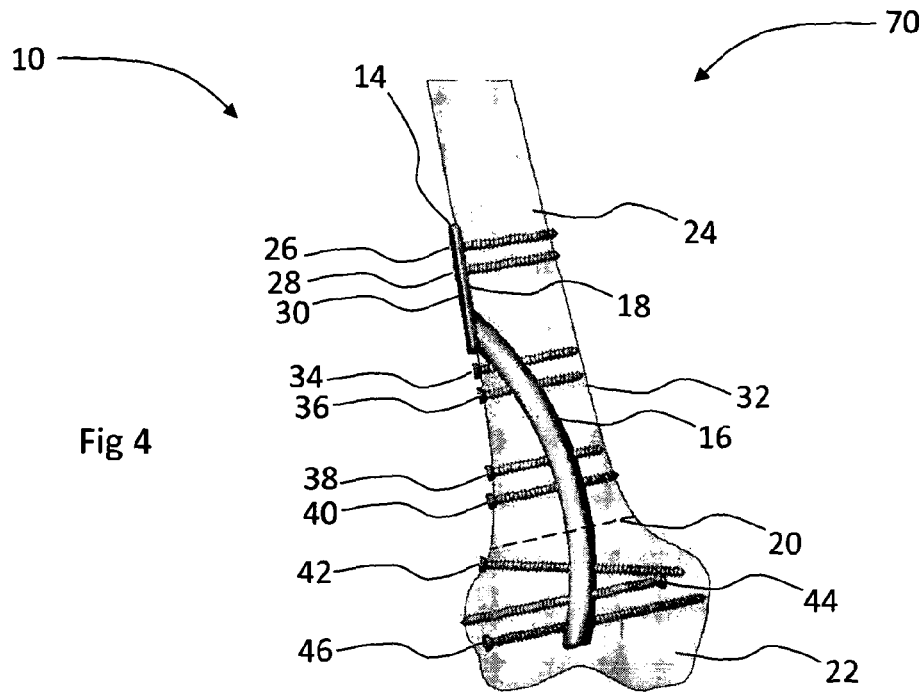
FIG. 4 shows a diagram of a surgical implant and a distal femur region according to an embodiment of the invention.

FIG. 4 shows a diagram of a surgical implant, generally designated 10, and a distal femur region, generally designated 70, according to an embodiment of the invention. In FIG. 4 like features to the arrangements of FIGS. 1, 2 and 3 are shown with like reference numerals. In FIG. 4 the elongate member 16 is shown to be positioned in the distal femur region 70 in an area spanning the Metaphysis region 32 and the Epiphysis region 22. The plate 14 is secured in the Diaphysis region 24 of the distal femur region 70 by two bone screws 26, 28 which pass through respective holes in the plate 14. A first portion of the elongate member 16 adjacent to the plate 14 has four holes for receiving four bone screws 34, 36, 38, 40 to secure the surgical insert 10 to the Metaphysis region 32. A second portion of the elongate member 16 adjacent to its free end has three holes for receiving three bone screws 42, 44, 46 to secure the surgical insert 10 to the Epiphysis region 22. In FIG. 4 it can be seen that the fracture 20 is located between the bone screws 34, 36, 38, 40 of the first portion, and the bone screws 42, 44, 46 of the second portion. The fracture 20 may be a Supracondylar fracture of the femur. Alternative fractures may be present as per the fractures 21, 23, 25, 27 of FIG. 1 which have been omitted from FIG. 4 for the purposes of clarity.

The elongate member 16 shown in FIG. 4 is about 80 mm in length, and the plate is about 30 mm in length so that the combined length of the elongate member 16 and the plate 14 is about 100 mm in length. The curve of the elongate member has a radius of curvature of about 110 mm. The curve is a single curve which lies in a single plane. The elongate member 16 is connected to the first surface 18 so that the plane of the curve is perpendicular to the plate 14. The elongate member 16 is connected to the first surface 18 so that a tangent of the curve of the elongate member 16 at the point of contact with the plate 14 is at an angle of 50°. In another arrangement the curved elongate member 16 lies in a single plane which is at an angle of between 5°-30° from the plate 14. This further assists with location of the insert 10 into the bone.

Figure 5:
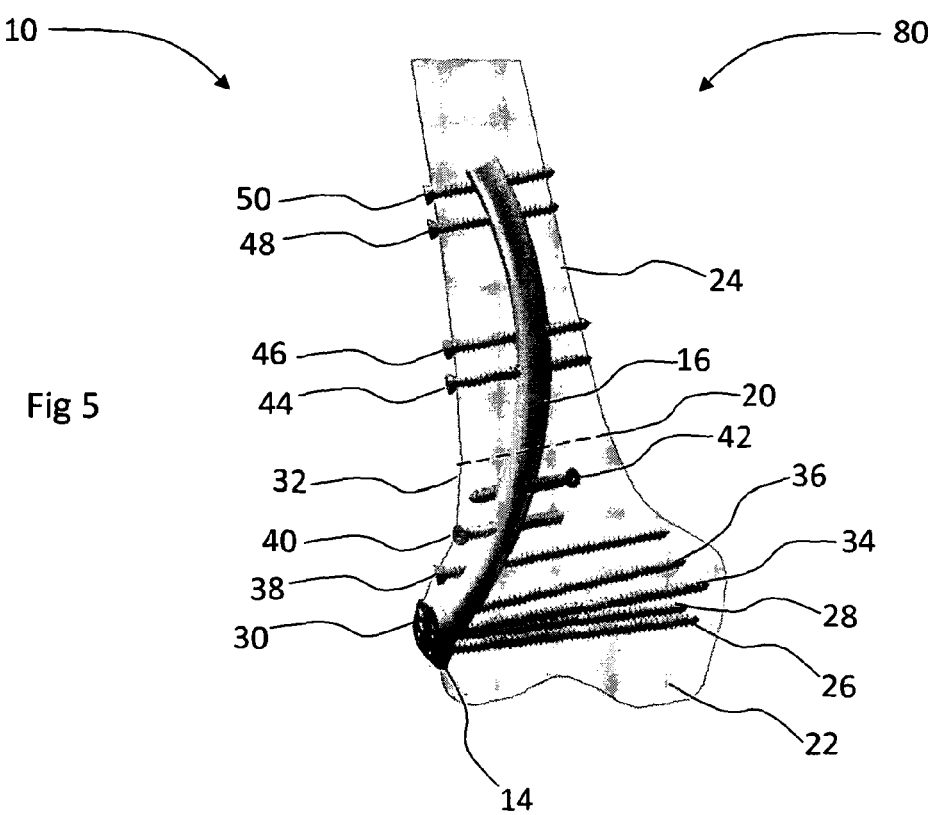
FIG. 5 shows a diagram of a surgical implant and a distal femur region according to another embodiment of the invention.

FIG. 5 shows a diagram of a surgical implant, generally designated 10, and a distal femur region, generally designated 80, according to another embodiment of the invention. In FIG. 5 like features to the arrangements of FIGS. 1-4 are shown with like reference numerals. In FIG. 5 the elongate member 16 is shown to be positioned in the distal femur region 80 in an area spanning the Metaphysis region 32 and the Epiphysis region 22. The plate 14 is secured in the Epiphysis region 22 of the distal femur region 80 by four bone screws 26, 28, 34, 36 which pass through respective holes in the plate 14. A first portion of the elongate member 16 adjacent to the plate 14 has three holes for receiving three bone screws 38, 40, 42 to secure the surgical insert 10 to the Metaphysis region 32. A second portion of the elongate member 16 adjacent to its free end has four holes for receiving four bone screws 44, 46, 48, 50 to secure the surgical insert 10 to the Diaphysis region 24. In FIG. 5 it can be seen that the fracture 20 is located between the bone screws 38, 40, 42 of the first portion, and the bone screws 44, 46, 48, 50 of the second portion. The fracture 20 may be a Supracondylar fracture of the femur. Alternative fractures may be present as per the fractures 21, 23, 25, 27 of FIG. 1 which have been omitted from FIG. 5 for the purposes of clarity.

The elongate member 16 shown in FIG. 5 is about 110 mm in length, and the plate is about 15 mm in length so that the combined length of the elongate member 16 and the plate 14 is about 115 mm in length. The curve of the elongate member has a radius of curvature of about 110 mm. The curve is a single curve which lies in a single plane. The elongate member 16 is connected to the first surface 18 so that the plane of the curve is perpendicular to the plate 14. The elongate member 16 is connected to the first surface 18 so that a tangent of the curve of the elongate member 16 at the point of contact with the plate 14 is at an angle of 50°. In another arrangement the curved elongate member 16 lies in a single plane which is at an angle of between 5°-30° from the plate 14. This further assists with location of the insert 10 into the bone.

Figure 6:
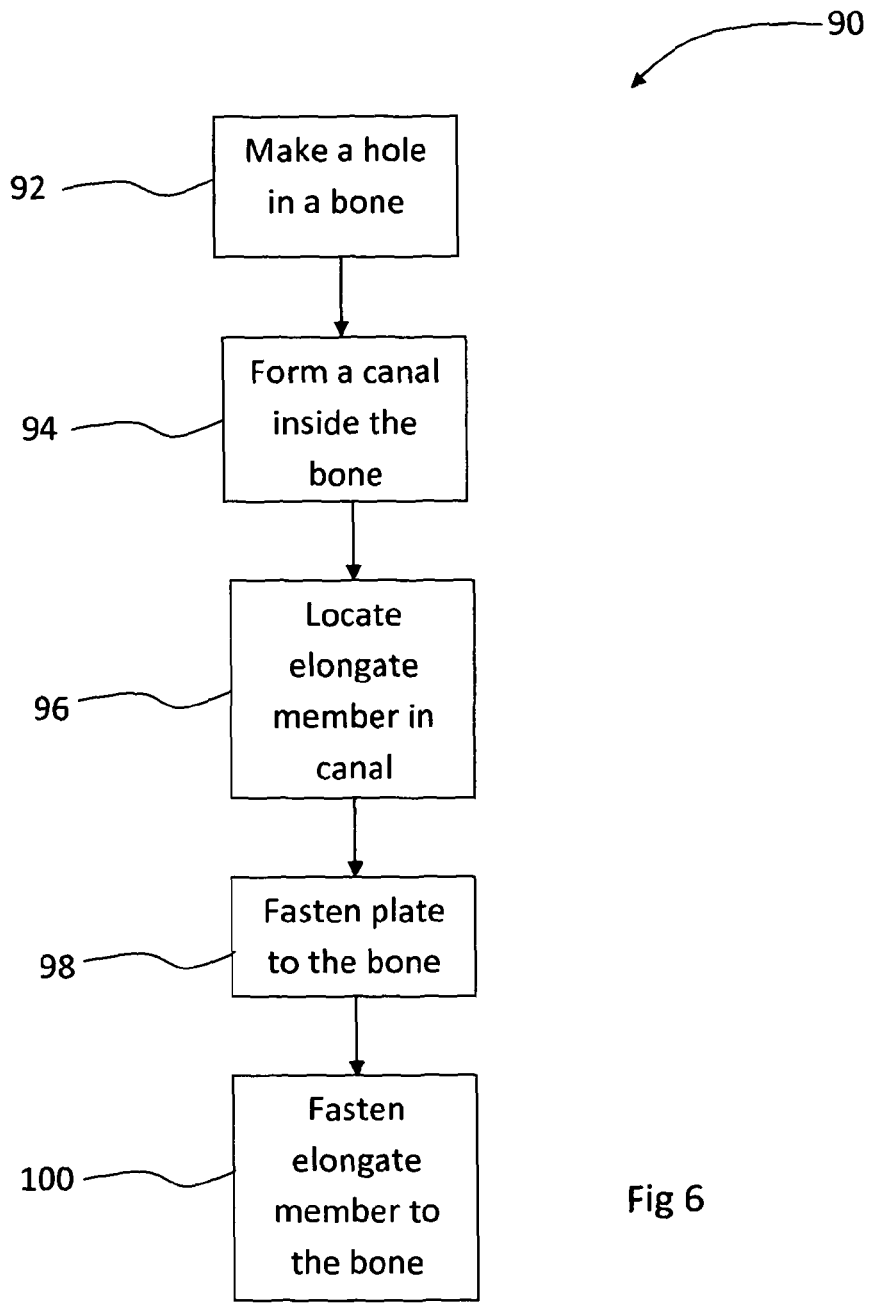
FIG. 6 shows steps of a method according to an embodiment of the invention.

FIG. 6 shows steps of a method according to an embodiment of the invention, generally designated 90. The surgical implant 10 of FIGS. 1-5 is positioned in substantially the same way for each location site. A hole in the bone is initially made in the surface of the bone, as shown at 92, and a canal is then formed inside the bone using known techniques, as shown at 94. Typically the canal is formed in the end area of the bone and extends up to about one third of the length of the bone. The elongate member 16 is then located through the hole in the bone and into the canal, as shown at 96 so that the plate 14 sits on the surface of the bone. It will be appreciated that the canal must be long enough to receive the elongate member 16 such that the plate 14 can be seated on a surface of the bone. Alternatively, a surgical implant 10 having a shorted elongate member 16 may be used. When the surgical implant 10 is located in position it is fixed in position to the bone. Such fixing is performed by firstly fastening the plate 14 to the surface of the bone, as shown at 98, using at least one bone screw 26, 28 which passes through the plate 14 and into the bone. The elongate member 16 is then fastened to the bone, as shown at 100, using at least one bone screw 34, 36, 38, 40, 42, 44, 46, 48, 50 which passes through the elongate member 16 and into the bone.

In the case of positioning the surgical implant in the proximal tibia region 12 shown in FIG. 1 the initial hole in the bone for inserting the elongate member 16 is made anterior-medially of the proximal tibial metaphysis approximately 80 mm from a tibial plateau. In the case of positioning the surgical implant in the distal tibia region 50 shown in FIG. 2 the initial hole in the bone for inserting the elongate member 16 is made anterior-medially of the distal tibial metaphysis approximately 70 mm from an articular surface. In the case of positioning the surgical implant in the proximal humerus region 60 shown in FIG. 3 the initial hole in the bone for inserting the elongate member 16 is made laterally of the proximal humeral metaphysis approximately 80 mm from an articular surface. In the case of positioning the surgical implant in the distal femur region 70 shown in FIG. 4 the initial hole in the bone for inserting the elongate member 16 is made laterally of the distal femur approximately 100 mm from an articular surface of the knee. In the case of positioning the surgical implant in the distal femur region 80 shown in FIG. 5 the initial hole in the bone for inserting the elongate member 16 is made laterally of the distal femur approximately 30-40 mm from an articular surface of the knee.

It will be appreciated that in FIGS. 1-4 the surgical implant 10 is positioned with the same orientation relative to an end of the bone such that the elongate member 16 extends towards the end of the bone. In contrast, in FIG. 5 the surgical implant 10 is positioned so that the elongate member 16 extends away from the end of the bone. It will also be appreciated that the method of inserting the surgical implant 10 shown in FIGS. 1-4 and FIG. 5 is similar in that a hole and canal must first be formed in a surface of the bone before inserting the elongate member 16 and securing the surgical implant with bone screws.

Figure 7:
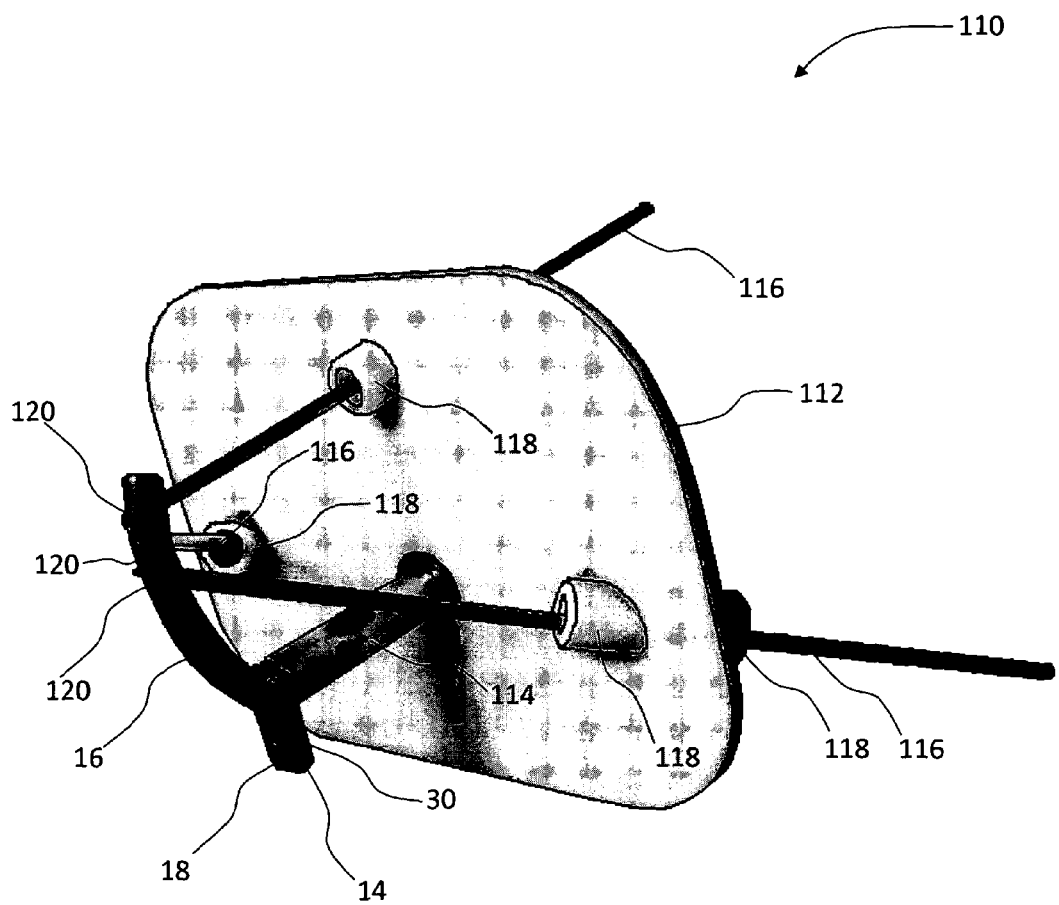
FIG. 7 shows a diagram of an external guide for the surgical implant shown in FIG. 3.

Such a surgical implant 10 and a method 90 for positioning it has the advantage that it can be inserted with minimal invasive surgery of the soft tissue surrounding the joint which preserves the biological substrate of the underlying fracture. Typically an initial incision of only 30 mm in the soft tissue is required to make a hole in the bone, to form the canal, to insert the elongate member 16 and to fasten the plate 14 to the bone. It will be appreciated that since the surgical implant 10 is about 70-130 mm in length it is easy to handle. Furthermore, since the surgical implant 10 is a unitary item there are no moving parts to operate, which is an advantageous feature. Overall the manner of positioning the surgical implant 10 and bone screws is straightforward when compared to the prior art. Alternatively surgical wire, percutaneous pins and/or transarticular pins may be used to secure the surgical implant 10 to the bone. It will be appreciated that the bone screws, the percutaneous pins and/or transarticular pins may be inserted with the use of an external guide, as shown in FIG. 7, so that the entry point for the fasteners can be accurately located or they may be inserted under arthroscopic monitoring or using an image intensifier. Furthermore, the canal formed in the bone may also be used to insert a bone graft into the bone for structural support if necessary, which provides a further advantage of utilising the canal for an additional purpose.

Whereas the surgical implant 10 of FIGS. 1-5 is shown to be connected to proximal or distal regions of different bones with five, nine or eleven bone screws, it will be appreciated that fewer bone screws may be needed to provide a suitable stabilisation of a bone fracture for it to heal. Furthermore, whereas the various fractures sites have been indicated in the FIGS. 1-5, it will be appreciated that these fracture sites may vary. The provision of up to eleven holes in the elongate member 16 with different orientations relative to the elongate member 16 provides versatility to use the surgical implant to treat different fracture sites. The orientation of the axis of each hole in the elongate member 16 may be between 0°-70° from a normal to the curved surface of the elongate member 16. Furthermore, at least one of the holes in each elongate member 16 may have an axis which is not located in the same plane as at least one other hole. The arrangement of the surgical implant 10 having a plurality of holes for receiving bone screws, and having the plate 14 and the elongate member 16 of different lengths allows it to be adapted to the anatomical peculiarities of the different anatomical sites. Together the bone screws and the surgical implant 10 form an intramedullary osteosythesis system for closed reduction and closed stabilisation of peri articular fractures.

It will be appreciated that the surgical implants 10 of FIGS. 1-5 are substantially the same in that they have a plate 14 and an elongate member 16, but with different dimensions for different applications. The surgical implant 10 described above may be manufactured from titanium as described above or any other suitable material for implantation into a human.

In the above described embodiments the holes for the bone screws 26, 28, 30, 32, 34, 36, 38, 40, 42, 44, 46, 48, 50 may be threaded holes. This provides the advantage that the bone screw 26, 28, 30, 32, 34, 36, 38, 40, 42, 44, 46, 48, 50 can be locked in position to the surgical implant.

FIG. 7 shows a diagram of an external guide for the surgical implant of FIG. 3, generally designated 110. In FIG. 7 features common the arrangements of FIG. 3 are shown with like reference numerals. In FIG. 7, the external guide 110 comprises a planar part 112 of a plastics material. The planar part 112 is rectangular in shape and has rounded corners, and has a length of about 200 mm, a width of about 150 mm, and a thickness of about 5 mm. The planar part 112 has a holding rod 114 bolted to it at one end of the holding rod 114 so that it is substantially perpendicular to the planar part 112. The holding rod 114 is detachably connected to the second surface 30 of the plate 14 in a region opposed to where the elongate member 16 projects from the first surface 18 of the plate 14. Such a detachable connection may be provided by a screw on the holding rod 114 and a corresponding threaded hole in the plate 14. The planar part 112 also has guide tubes 118 which pass through the planar part 112 at a pre-defined orientation relative to the planar part 112. Each guide tube 118 is for receiving a pin 116 so that it is guided to a respective hole 120 in the elongate member 16. Using pins 118 in this manner is a precursor to using bone screws to secure the surgical implant to a bone. It will be appreciated that using the external guide 110 may assist the orthopaedic surgeon in positioning the surgical implant within a bone and to secure it to the bone to stabilise a bone fracture. Whereas the external guide for the surgical implant of FIG. 3 has been described, similar external guides may be used for the surgical implants of FIGS. 1, 2, 4, 5, 8-12, 13, 14-17 and 18.

Figure 8:
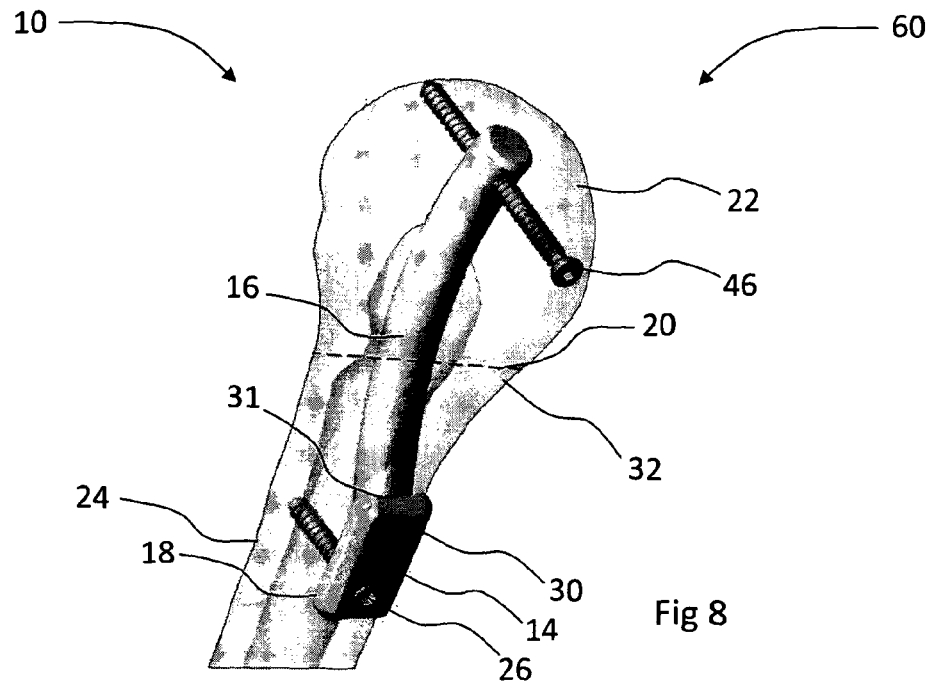
FIGS. 8-12 show a diagram of a surgical implant and a proximal humerus region according to an embodiment of the invention.

FIGS. 8-13 show a diagram of a surgical implant, generally designated 10, and a proximal humerus region, generally designated 60, according to embodiments of the invention. In FIGS. 8-13 like features to the arrangements of FIG. 3 are shown with like reference numerals. In FIG. 8 the elongate member 16 is shown to be positioned in the proximal humerus region 60 in an area spanning the Metaphysis region 32 and the Epiphysis region 22. The plate 14 is secured in the Diaphysis region 24 of the proximal humerus region 60 by one bone screw 26 which passes through a hole in the plate 14. The elongate member 16 has one hole substantially at the free end of it for receiving one bone screw 46 to secure the elongate member 16 to the Epiphysis region 22. The single hole is about 2-7 mm away from the free end of the elongate member 16, and preferably substantially 5 mm from the free end of the elongate member 16. In FIG. 8 it can be seen that the fracture 20 is located approximately in the middle of the elongate member 16. The fracture 20 may be a proximal humerus to humerus head fracture. Alternative fractures may be present as per the fractures 21, 23, 25, 27 of FIG. 1 which have been omitted from FIG. 8 for the purposes of clarity.

FIG. 8 also shows that the second surface 30 of the plate 14 is flat and the first surface 18 of the plate 14 is curved as shown at 31. The curved first surface 18 is a concave surface of the plate 14 and is a single curved surface having a radius of curvature of about 10-20 mm. The curved first surface 18 is advantageous because it confirms to the surface of the Diaphysis region 24 of the bone and assists with location of the surgical implant 10.

Figure 9:
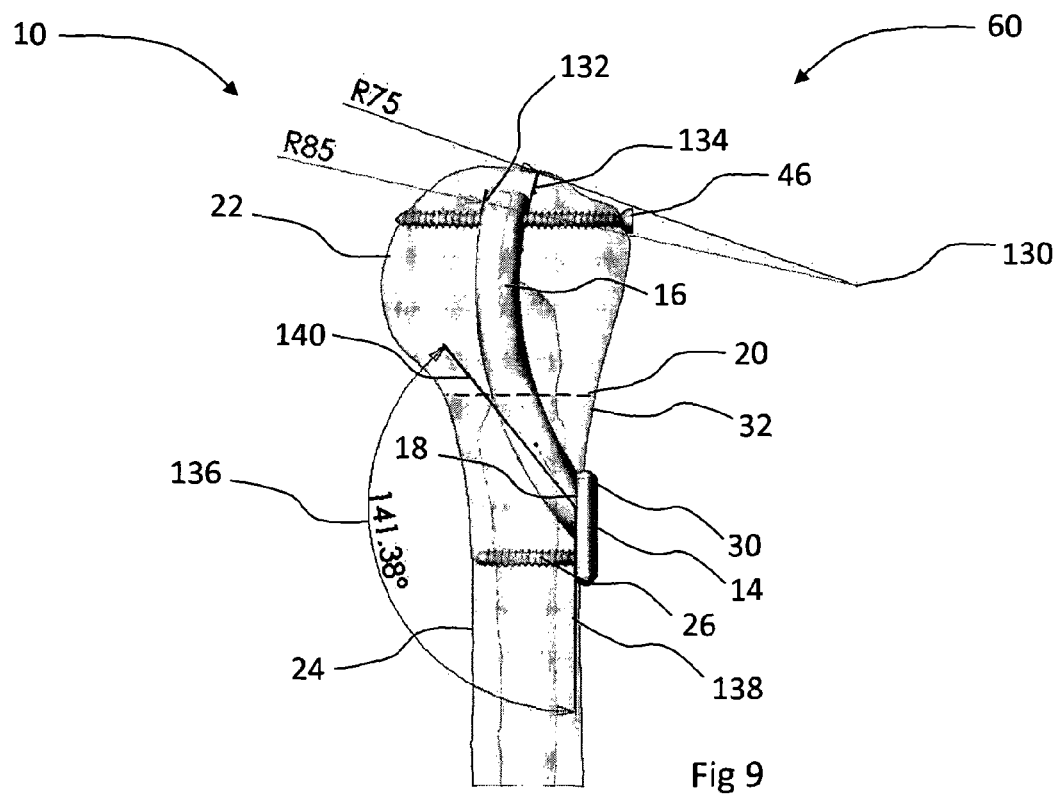

The elongate member 16 shown in FIGS. 8-13 is about 90 mm in length, and the plate is about 30 mm in length so that the combined length of the elongate member 16 and the plate 14 is about 110 mm in length. The curve of the elongate member 16 is an arc of a circle and has a radius of curvature of about 80 mm as shown in FIG. 9 about a point 130. The elongate member 16 is a solid bar having a diameter of 10 mm, and it will be appreciated that the curve of the elongate member 16 has an outer periphery 132 and an inner periphery 134. The radius of curvature of the outer periphery 132 is 85 mm, and the radius of curvature of the inner periphery is 75 mm. Also shown in FIG. 9 is an obtuse angle 136 which is between a plane 138 containing the plate 14, and a tangent 140 of the curved elongate member 16 at the point of contact with the first surface of the plate 14. The tangent 140 projects from the plate 14 in a plane containing the elongate member 16. The angle 136 is shown to be substantially 141°, although it will be appreciated that an angle 136 of 135°-147° may also be used. It will be appreciated that the view in FIG. 9 shows the plane 138 substantially end-on so that it is represented by the single line 138.

Figure 10:
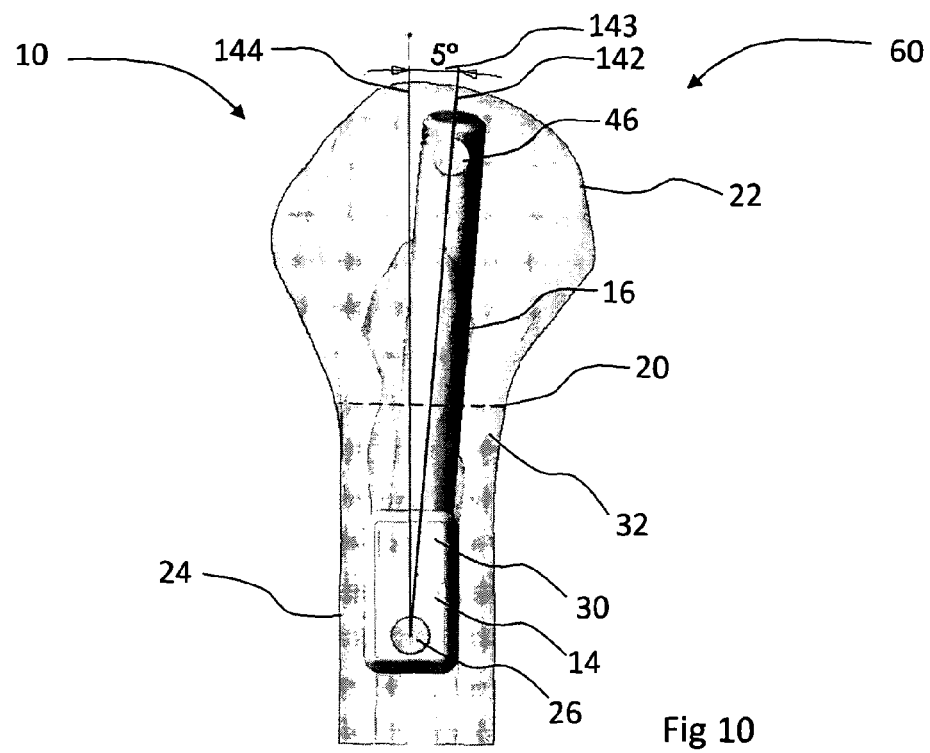

FIG. 10 shows the curved elongate member 16 lying in a plane 142 which is perpendicular to the plate 14. Also shown is another plane 144 which is perpendicular to the plate 14 and which is aligned with a longitudinal axis of the plate 14. The planes 142 and 144 are at an angle 143 of substantially 5° to each other so that they intersect at the point of contact of the plate 14 and the elongate member 16. It will be appreciated that the angle 143 may be in the range 3°-7°. The view in FIG. 10 shows the planes 142, 144 substantially end-on so that they are represented by the single lines 142, 144. The angle 143 is advantageous because it allows the plate 14 to be aligned with the bone so that the curved surface 31 of the plate 14 sits on the Diaphysis region 24 of the bone, whilst the free end of the elongate member 16 is located in the Epiphysis region 22 of the bone. Overall the angle 143 between the planes 142, 144 assists with location of the surgical implant 10.

In another arrangement the plane 142 is not perpendicular to the plate 14 but lies at an angle of between 5°-30° from the plate 14. In this arrangement the plane 142 is also at an angle of between 3°-7°, and preferably 5°, from the longitudinal axis of the plate 14 which is in the plane 144. Such a defined projection of the curved elongate member 16 from the plate 14 is advantageous because it permits the free end to be located in the Epiphysis region 22 more easily.

Figure 11:
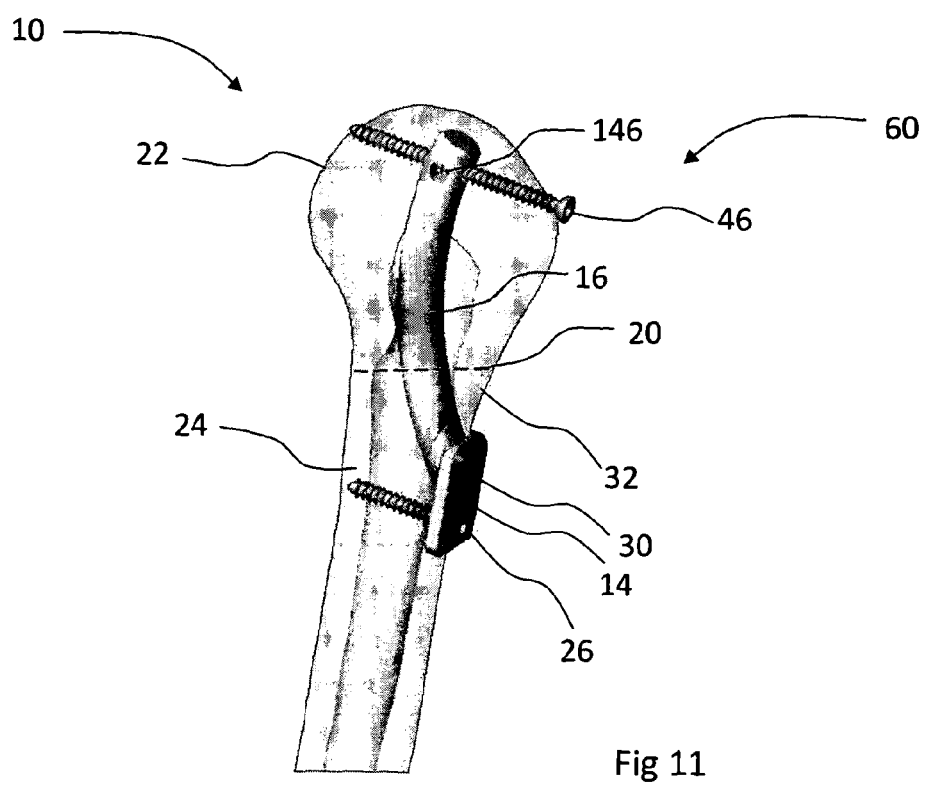
Figure 12:
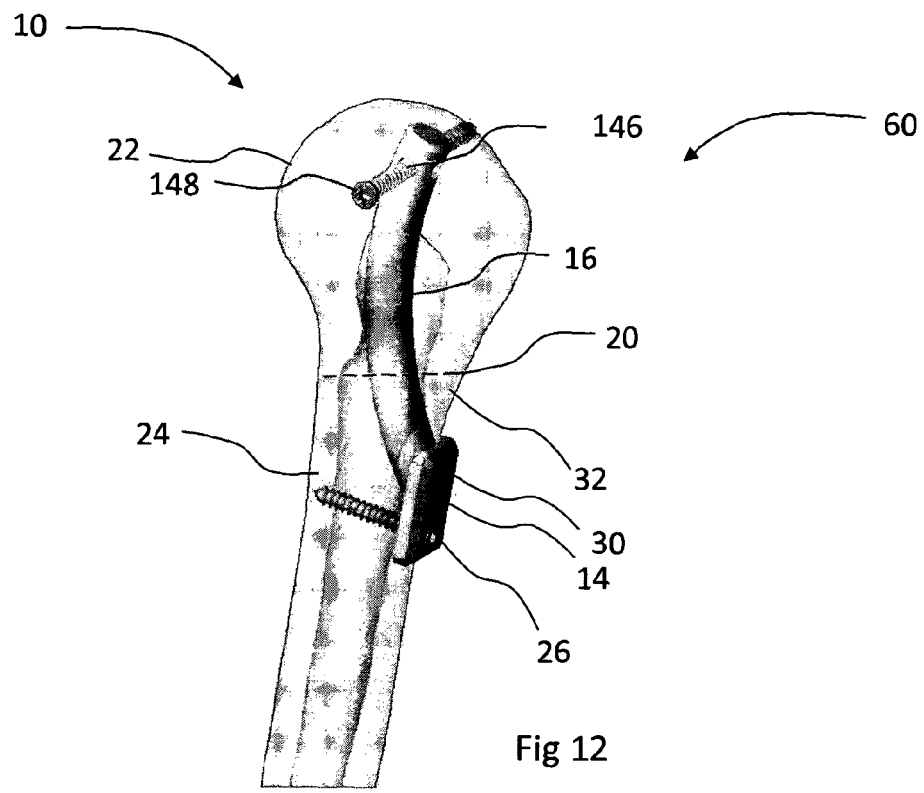

FIG. 11 shows a modified version of the arrangement of FIGS. 8-10 whereby the free end of the elongate member 16 is provided with two holes that intersect as shown at 146. One hole has an axis which lies in the plane 142 of the curved elongate member 16. The other hole has an axis which is substantially perpendicular to the plane 142. One or both holes may have an axis which is perpendicular to the elongate member 16. In another embodiment one or both holes have an axis which is slightly away from perpendicular to the elongate member 16, for example 85° to the elongate member 16. The intersecting holes 146 are advantageous because they permit a surgeon fitting the implant 10 to use a fastening region substantially at the end of the elongate member 16 whilst allowing an alternative angle for inserting a fastener 46 as shown in FIG. 12. As shown in FIGS. 11 and 12 the intersecting holes 146 have axes which are substantially 90° to each other. The two holes intersecting each other may be thought of as one fastening region comprising the two intersecting holes.

Figure 13:
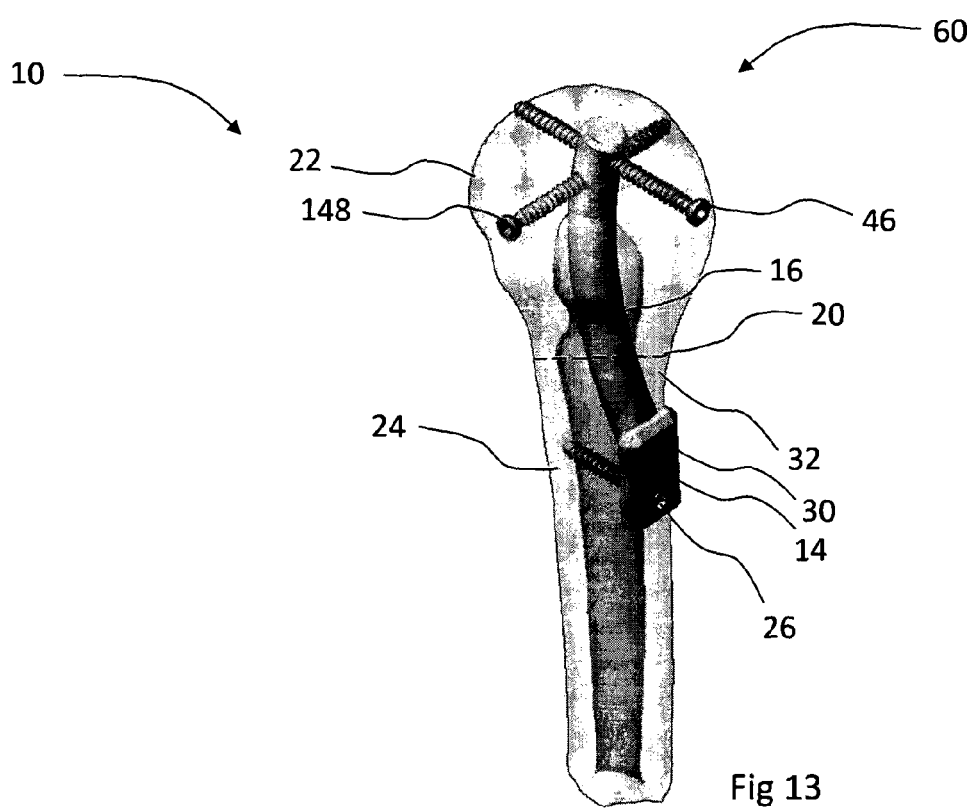
FIG. 13 shows a diagram of a surgical implant and a proximal humerus region according to an embodiment of the invention.

FIG. 13 shows a diagram of a surgical implant, generally designated 10, and a proximal humerus region, generally designated 60, according to an embodiment of the invention. In FIG. 13 like features to the arrangements of FIGS. 8-12 are shown with like reference numerals. In FIG. 13 the free end of the elongate member 16 is shown to be secured to the Epiphysis region 22 by two fasteners 46, 148 which pass through two respective holes at the free end of the elongate member 16. The holes are about 2-7 mm away from the free end of the elongate member 16, and preferably substantially 5 mm from the free end of the elongate member 16. The holes do not intersect each other and have respective axes which are substantially perpendicular. Such an arrangement permits the surgeon to use two fasteners 46, 148 if appropriate instead of the arrangement of FIGS. 11 and 12 where only one fastener can be used.

The arrangements of the surgical implant 10 shown in FIGS. 8-13 with the defined angle 136 of substantially 141°, and a radius of curvature of the elongate member 16 of substantially 80 mm, and/or the defined angle 143 of the plane 142 relative to the plane 144 of substantially 5°, and/or the single fastener 46 and/or intersecting holes at the free end of the elongate member 16 are advantageous because they permit the elongate member 16 to be inserted in the proximal humerus with accuracy and taking into account the manner of insertion of the elongate member 16 and the anatomy of the bone in which the elongate member 16 is being inserted.

Figure 14:
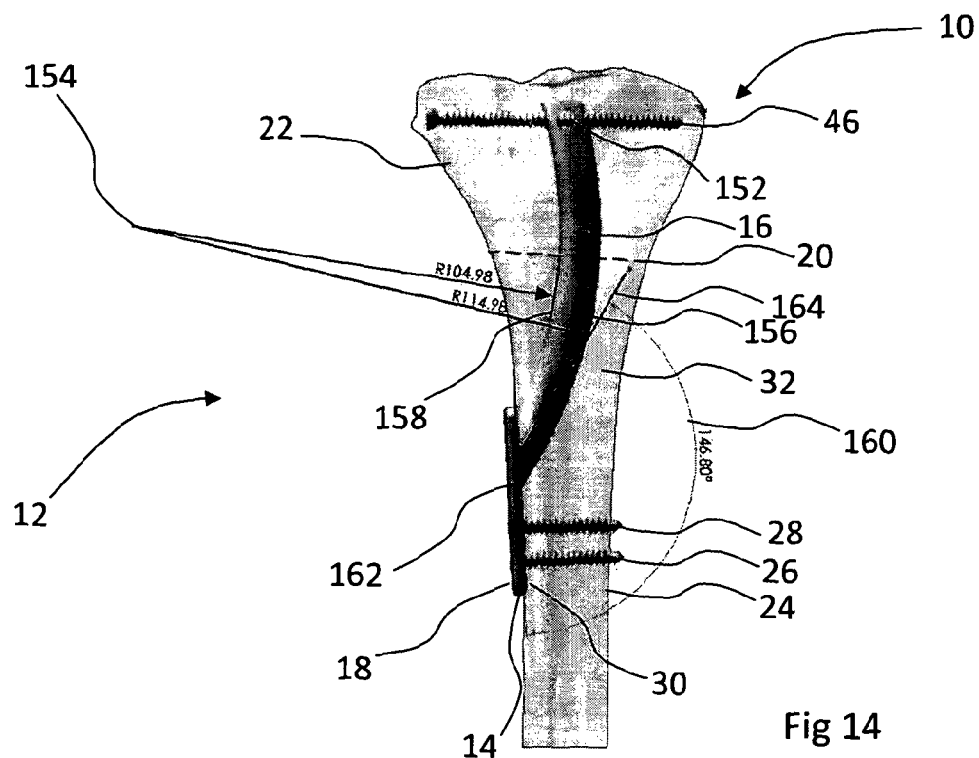
FIGS. 14-17 show a diagram of a surgical implant and a proximal tibia region according to an embodiment of the invention.
Figure 15:
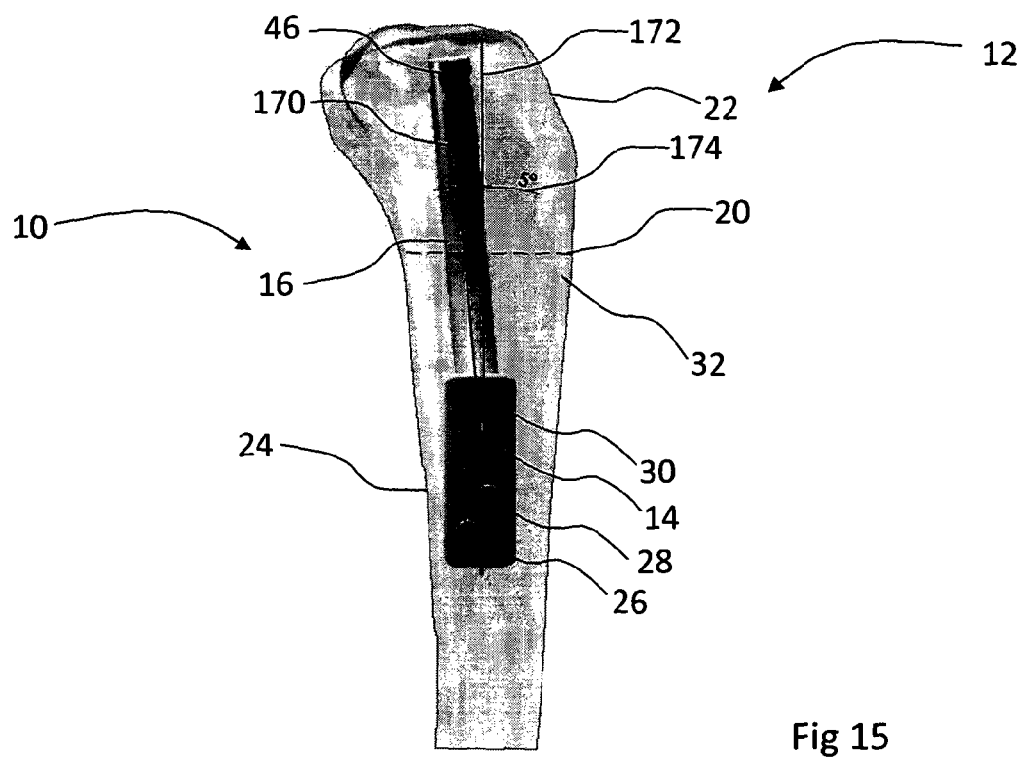
Figure 16:
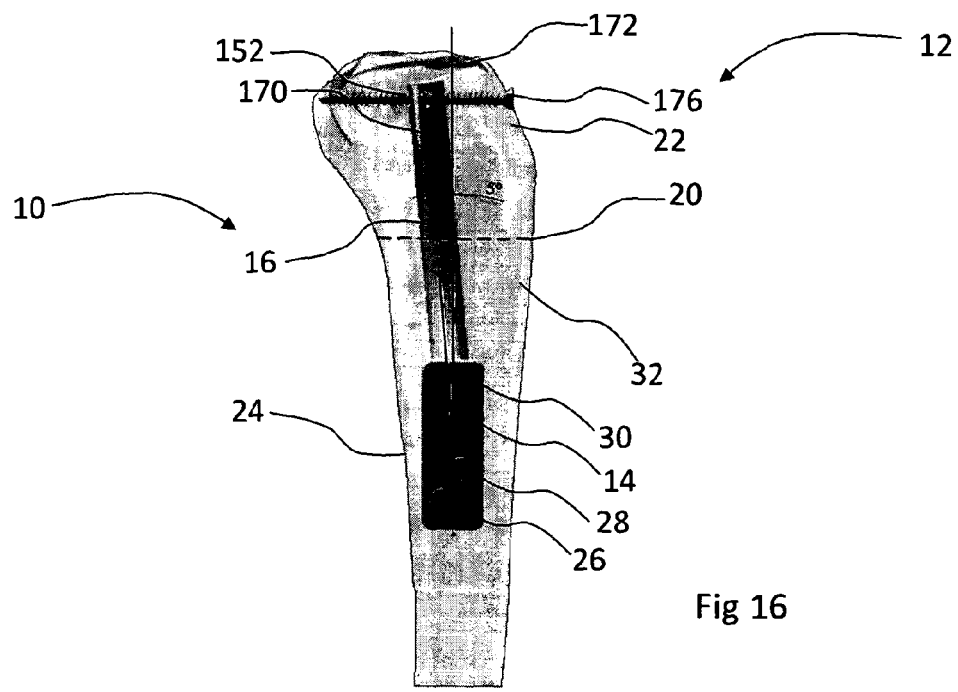

FIGS. 14-18 show a diagram of a surgical implant, generally designated 10, and a proximal tibia region, generally designated 12, according to embodiments of the invention. In FIGS. 14-18 like features to the arrangements of FIG. 1 are shown with like reference numerals. In FIG. 14 the elongate member 16 is shown to be positioned in the proximal tibia region 12 in an area spanning the Metaphysis region 32 and the Epiphysis region 22. The plate 14 is secured in the Diaphysis region 24 of the proximal tibia region 12 by two bone screws 26, 28 which pass through respective holes in the plate 14. The elongate member 16 has two holes substantially at the free end of it generally shown at 152, which intersect each other. One hole has an axis which lies in the plane 170 (shown in FIG. 15) of the curved elongate member 16. The other hole has an axis which is substantially perpendicular to the plane 170. The two holes intersecting each other may be thought of as one fastening region comprising the two intersecting holes. The two holes 152 are for receiving one bone screw 46 to secure the elongate member 16 to the Epiphysis region 22. The two holes are about 2-7 mm away from the free end of the elongate member 16, and preferably about 5 mm from the free end of the elongate member 16. One or both holes may have an axis which is perpendicular to the elongate member 16. In another embodiment one or both holes have an axis which is slightly away from perpendicular to the elongate member 16, for example 85° to the elongate member 16. The intersecting holes 152 are advantageous because they permit a surgeon fitting the implant 10 to use a fastening region substantially at the end of the elongate member 16 whilst allowing an alternative angle for inserting a fastener 46 as shown in FIGS. 14 and 16. As shown in FIGS. 14 and 16 the intersecting holes 152 have axes which are substantially 90° to each other.

In FIG. 14 it can be seen that the fracture 20 is located approximately in the middle of the elongate member 16. Alternative fractures may be present as per the fractures 21, 23, 25, 27 of FIG. 1 which have been omitted from FIG. 14 for the purposes of clarity.

Figure 17:
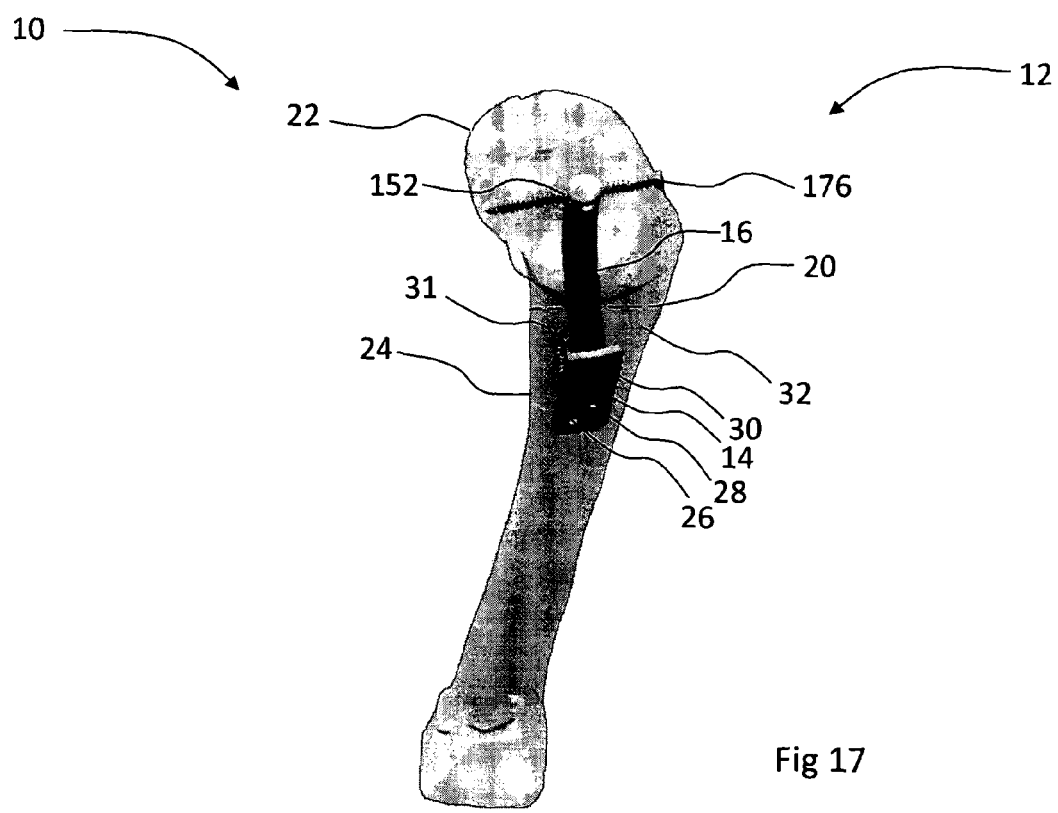

FIG. 17 also shows that the second surface 30 of the plate 14 is flat and the first surface 18 of the plate 14 is curved as shown at 31. The curved first surface 18 is a concave surface of the plate 14 and is a single curved surface having a radius of curvature of about 10-20 mm. The curved first surface 18 is advantageous because it confirms to the surface of the Diaphysis region 24 of the bone and assists with location of the surgical implant 10.

The elongate member 16 shown in FIGS. 14-18 is about 60 mm in length, and the plate is about 28 mm in length so that the combined length of the elongate member 16 and the plate 14 is about 88 mm in length. As shown in FIG. 14 the curve of the elongate member 16 is an arc of a circle that has a radius of curvature of about 110 mm about a point 154. The elongate member 16 is a solid bar having a diameter of 10 mm, and has an outer periphery 156 and an inner periphery 158. The radius of curvature of the outer periphery 156 is about 115 mm, and the radius of curvature of the inner periphery 158 is about 105 mm. Also shown in FIG. 14 is an obtuse angle 160 which is between a plane 162 containing the plate 14, and a tangent 164 of the elongate member 16 at the point of contact with the first surface of the plate 14. The tangent 164 projects from the plate 14 in a plane containing the elongate member 16. The obtuse angle 160 is shown to be substantially 147°, although the angle 160 may be in the range 141°-153°. It will be appreciated that the view in FIG. 14 shows the plane 162 substantially end-on so that it is represented by the single line 162.

FIG. 15 shows the curved elongate member 16 lying in a plane 170 which is perpendicular to the plate 14. Also shown is another plane 172 which is perpendicular to the plate 14 and which is aligned with a longitudinal axis of the plate 14. The planes 170 and 172 are at an angle 174 of substantially 5° to each other so that they intersect at the point of contact of the plate 14 and the elongate member 16. It will be appreciated that the angle 174 may be in the range 3°-7°. The view in FIG. 15 shows the planes 170, 172 substantially end-on so that they are represented by the single lines 170, 172. The angle 174 is advantageous because it allows the plate 14 to be aligned with the bone so that the curved surface 31 of the plate 14 sits on the Diaphysis region 24 of the bone, whilst the free end of the elongate member 16 is located in the Epiphysis region 22 of the bone. Overall the angle 174 between the planes 170, 172 assists with location of the surgical implant 10.

In another arrangement the plane 170 is not perpendicular to the plate 14 but lies at an angle of between 5°-30° from the plate 14. In this arrangement the plane 170 is also at an angle of between 3°-7°, and preferably 5°, from the longitudinal axis of the plate 14 which is in the plane 172.

FIG. 16 shows the free end of the surgical implant 10 fastened to the bone using a different screw 176 which is inserted through one of the two intersecting holes 152. In FIG. 16 it can be seen that the screw 176 is substantially perpendicular to the screw 46 shown in FIG. 15.

Figure 18:
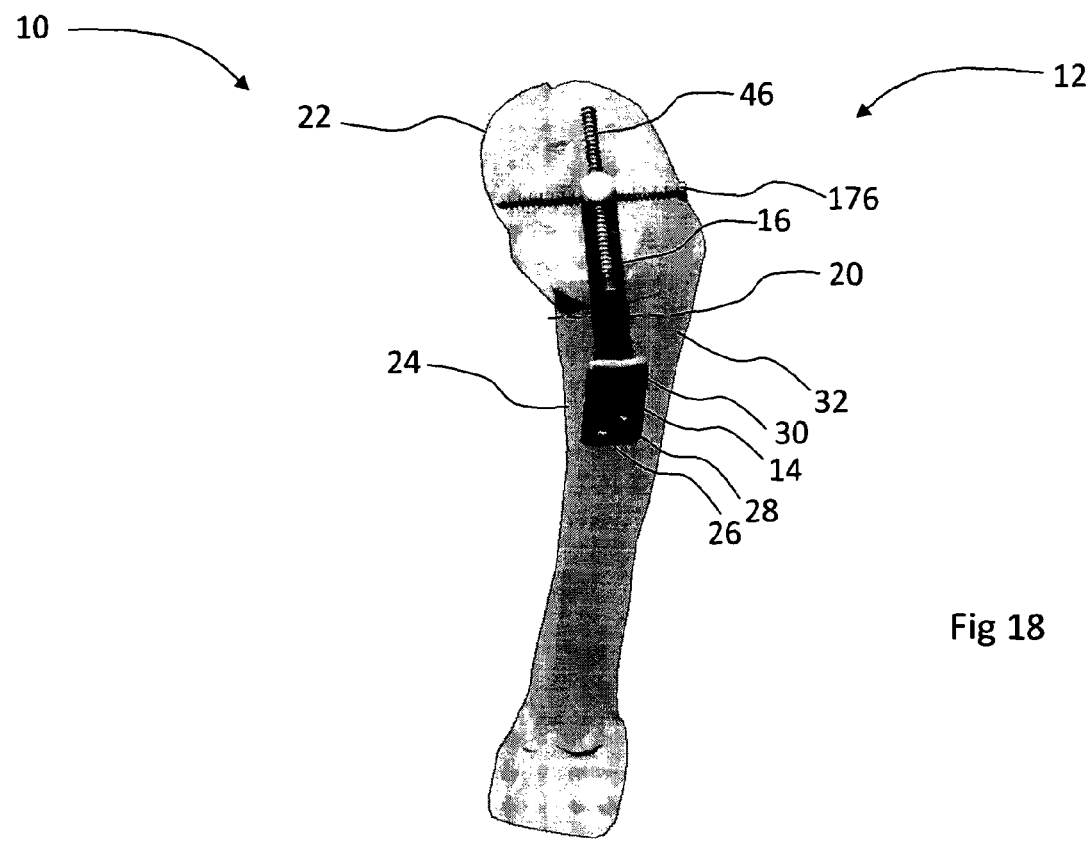
FIG. 18 shows a diagram of a surgical implant and a proximal tibia region according to an embodiment of the invention.

FIG. 18 shows a diagram of a surgical implant, generally designated 10, and a proximal tibia region, generally designated 12, according to an embodiment of the invention. In FIG. 18 like features to the arrangements of FIGS. 14-17 are shown with like reference numerals. In FIG. 18 the free end of the elongate member 16 is shown to be secured to the Epiphysis region 22 by two fasteners 46, 176 which pass through two respective holes at the free end of the elongate member. The holes are about 2-7 mm away from the free end of the elongate member 16, and preferably substantially 5 mm from the free end of the elongate member 16. The holes do not intersect each other and have respective axes which are substantially perpendicular. Such an arrangement permits the surgeon to use two fasteners 46, 176 if appropriate instead of the arrangement of FIGS. 14-17 where only one fastener can be used.

The arrangements of the surgical implant 10 shown in FIGS. 14-18 with the defined angle 160 of substantially 147°, and a radius of curvature of the elongate member 16 of substantially 110 mm, and/or the defined angle 174 of the plane 170 relative to the plane 172 of substantially 5°, and/or the single fastener 46 and/or intersecting holes 152 at the free end of the elongate member 16 are advantageous because they permit the elongate member 16 to be inserted in the proximal tibia with accuracy and taking into account the manner of insertion of the elongate member 16 and the anatomy of the bone in which the elongate member 16 is being inserted.

It will be appreciated that the elongate member 16 of the above described embodiments is curved along its whole length. It also has a radius of curvature which is relatively large to allow it to be inserted into the bone so that an envelope of the elongate member 16 is substantially within the bone. Furthermore, the relatively large radius of the curved elongate member 16 allows the free end to be inserted in awkward to reach parts of the Epiphysis region 22.

It will further be appreciated in the embodiments above that the at least one hole in the elongate member 16 may have an axis that is not perpendicular to the surface of the elongate member 16. For example, the axis of the at least one hole in the elongate member 16 may be between 30-85° from the surface of the elongate member 16.

In the above embodiments the elongate member 16 may have a length of between 40-130 mm. The elongate member 16 may have a length provided in approximately 5 mm increments between 40-130 mm such that it is about 40 mm, 45 mm, 50 mm, 55 mm, 60 mm, 65 mm, 70 mm, 75 mm, 80 mm, 85 mm, 90 mm, 95 mm, 100 mm, 105 mm, 110 mm, 115 mm, 120 mm, 125 mm, or 130 mm in length. In one embodiment a plurality of surgical implants 10 are provided as a kit whereby the elongate member 16 of each surgical implant has a length of between 40-130 mm, and at least two of the surgical implants 10 in the kit have an elongate member 16 which differs in length by about 5 mm, or 4-6 mm, or 10 mm. This is a useful feature because it allows a surgeon to select the surgical implant 10 having the most appropriate length for location in a particular region of a particular bone, which may vary from person to person.

The invention claimed is:

1. A surgical implant for a bone fracture comprising a plate and an elongate member projecting from the plate, the elongate member for insertion into a bone and the plate for attachment to a surface of a bone, each of the elongate member and the plate are provided with at least one fastening region for securing the surgical implant to a bone, wherein the elongate member comprises at least a portion that is curved, and the curved portion is a single curve lying in a single plane, wherein the elongate member projects from the plate such that the single plane is at an angle of between 5°-30° from the plate, and wherein the single plane is also at an angle of between 3°-7° from another plane which is perpendicular to the plate, said another plane being aligned with a longitudinal axis of the plate.

2. A surgical implant according to claim 1, wherein the curved portion is an arc of a circle or an ellipse.

3. A surgical implant according to claim 1, wherein the curved portion has a radius of curvature of between 45-130 mm.

4. A surgical implant according to claim 1, wherein the elongate member is between 40-130 mm in length.

5. A surgical implant according to claim 1, wherein at least one of the fastening regions is a through hole for receiving a fastener.

6. A surgical implant according to claim 5, wherein the elongate member includes at least two through holes.

7. A surgical implant according to claim 6, wherein the at least two through holes have respective axes which are non-parallel.

8. A surgical implant according to claim 5, wherein at least one through hole is in the elongate member and has an axis which is between 0°-70° from a normal to the elongate member.

9. A surgical implant according to claim 8, wherein at least one through hole is in the elongate member and has an axis which is between 5°-70° from a normal to the elongate member.

\* \* \* \* \*